United States Patent
Yang et al.

(10) Patent No.: US 10,307,219 B2
(45) Date of Patent: Jun. 4, 2019

(54) NONINVASIVE STEREOTACTIC ASSEMBLY

(71) Applicant: NATIONAL CHIAO TUNG UNIVERSITY, Hsinchu (TW)

(72) Inventors: Bing-Shiang Yang, Hsinchu (TW); Yu-Hsiang Hao, Taoyuan (TW)

(73) Assignee: National Chiao Tung University, Hsinchu (TW)

( * ) Notice: Subject to any disclaimer, the term of this patent is extended or adjusted under 35 U.S.C. 154(b) by 258 days.

(21) Appl. No.: 15/591,828

(22) Filed: May 10, 2017

(65) Prior Publication Data

US 2018/0168766 A1 Jun. 21, 2018

(30) Foreign Application Priority Data

Dec. 20, 2016 (TW) .............................. 105142174 A (51) Int. Cl.
*A61B 90/10* (2016.01)
*A61B 90/14* (2016.01)
*A61B 90/11* (2016.01)

(52) U.S. Cl.
CPC .............. *A61B 90/10* (2016.02); *A61B 90/11* (2016.02); *A61B 90/14* (2016.02)

(58) Field of Classification Search
CPC ......... A61B 90/10; A61B 90/11; A61B 90/16; A61B 90/14; A61B 2090/101; A61B 2090/103; A61B 34/20; A61B 34/30
USPC ........................................................ 606/130
See application file for complete search history.

(56) References Cited

U.S. PATENT DOCUMENTS

| | | | |
|---|---|---|---|
| 5,423,832 A | 6/1995 | Gildenberg | |
| 5,702,406 A | 12/1997 | Vilsmeier et al. | |
| 5,855,582 A | 1/1999 | Gildenberg | |
| 6,080,164 A | 6/2000 | Oshio et al. | |
| 8,613,714 B2 | 12/2013 | Alleman et al. | |
| 2008/0269777 A1* | 10/2008 | Appenrodt | A61N 1/0529 606/130 |

(Continued)

FOREIGN PATENT DOCUMENTS

| TW | I386189 B1 | 2/2013 |
|---|---|---|
| TW | 201438673 A | 10/2014 |

(Continued)

OTHER PUBLICATIONS

Kyriaki Theodorou, Constantin Kappas & Constantin Tsokas. "A new non-invasive and relocatable immobilization frame for fractionated stereotactic radiotherapy." Radiotherapy and Oncology 47 (1998) 313-317.

*Primary Examiner* — Diane D Yabut
*Assistant Examiner* — Majid Jamialahmadi
(74) *Attorney, Agent, or Firm* — Quinn IP Law (57) ABSTRACT

A noninvasive stereotactic assembly for guiding an instrument to a target within a patient's head includes a head frame subassembly and an instrument positioning subassembly. The head frame subassembly is secured to a skull in the patient's head to determine an X-axis and a Y-axis of a three-dimensional coordinate system. According to the coordinate of the target in the three-dimensional coordinate system, ring members, a movable bracket, a swivel member, and an instrument holder of the instrument positioning subassembly are displaced by predetermined angles to guide the instrument toward the target.

6 Claims, 8 Drawing Sheets

(56) References Cited

U.S. PATENT DOCUMENTS

2015/0230871 A1\* 8/2015 Sayler .................... A61B 5/702
  128/845

FOREIGN PATENT DOCUMENTS

| TW | M503195 U | 6/2015 |
| TW | M503196 U | 6/2015 |

\* cited by examiner

NONINVASIVE STEREOTACTIC ASSEMBLY

CROSS-REFERENCE TO RELATED APPLICATION

This application claims priority from Taiwanese patent application no. 105142174, filed on Dec. 20, 2016.

FIELD

The disclosure relates to a stereotactic assembly, more particularly to a noninvasive stereotactic assembly for guiding an instrument to a target within a patient's head.

BACKGROUND

U.S. Pat. No. 5,423,832 discloses a conventional positioning apparatus for interrelating the positions of a noninvasive stereoadapter used in performing presurgical diagnostic procedures and an invasive stereotactic heading apparatus used in performing surgical or other treatment procedures.

Another noninvasive steroadapter is disclosed by Kyriaki Theodorou et al., "A new non-invasive and relocatable immobilization frame for fractionated stereotactic radiotherapy," Radiotherapy and Oncology 47 (1998) 313-317.

Likewise, U.S. Pat. Nos. 5,855,582, 5,702,406, 6,080, 164, and 8,613,714 also disclose non-invasive stereotactic devices.

A stereotactic navigation system for navigating an instrument to a target within a patient, as disclosed in U.S. Pat. No. 7,925,328, may include a stereotactic head frame, an imaging device, a tracking device, a controller and a display. The stereotactic head frame is coupled to the patient and is used to assist in guiding the instrument to the target. The imaging device captures image data of the patient and of the stereotactic head frame. The controller receives the image data from the imaging device and identifies the stereotactic head frame in the image data and automatically registers the image data with navigable patient space upon identifying the stereotactic head frame, while the display displays the image data.

SUMMARY

An object of the disclosure is to provide a novel noninvasive stereotactic assembly for guiding an instrument to a target within a patient's head. With the provision of the novel noninvasive stereotactic assembly, the instrument can be precisely guided toward the target.

According to the disclosure, a noninvasive stereotactic assembly for guiding an instrument to a target within a patient's head is disclosed. The patient's head includes a nasion and left and right temporal bones. The target has a coordinate determined by a three-dimensional coordinate system of image data of the patient's head. The instrument defines a lengthwise line which is initially oriented along a Z-axis toward an origin of the three-dimensional coordinate system. The stereotactic assembly includes a head frame subassembly and an instrument positioning subassembly. The head frame subassembly includes a pair of seat blocks, a pair of adjustable pin members, a nasion positioning member, a pair of cantilever units, and a pair of adjusting units. The seat blocks are spaced apart from each other in a left-and-right direction. Each of the seat blocks has left and right surfaces and is formed with a guiding slot which extends through the left and right surfaces. The adjustable pin members are slidably and respectively mounted in the guiding slots of the seat blocks, and have respectively left and right pointed ends which are adapted to be brought into rigid engagement with the left and right temporal bones, respectively, so as to cooperatively define an X-axis of the three-dimensional coordinate system. The nasion positioning member includes a beam body and a nasion pad. The beam body extends in the left-and-right direction to terminate at left and right actuated end segments. The nasion pad is mounted on a mid segment of the beam body between the left and right actuated end segments, and has a mid area adapted to be brought into rigid engagement with the nasion of the patient, and an index protrusion opposite to and in line with the mid area in an anterior-and-posterior direction, such that when the mid area is in rigid engagement with the nasion of the patient, the index protrusion and the mid area cooperatively defines a Y-axis of the three-dimensional coordinate system, which intersects with the X-axis to define the origin. Each of the cantilever units includes a cantilever block secured to a corresponding one of the seat blocks, and a cantilever arm which extends from the cantilever block in the anterior-and-posterior direction, and which is configured to permit a corresponding one of the left and right actuated end segments to be adjustably moved along the anterior-and-posterior direction. Each of the adjusting units is coupled to a corresponding one of the adjustable pin members so as to permit the adjustable pin members to move toward or away from each other. The instrument positioning subassembly includes two ring members, a bridging rail member, a movable bracket, a swivel member, and an instrument holder. The two ring members are mounted rotatably on and outboard of the seat blocks about the X-axis, respectively. According to the coordinate of the target, the two ring members are simultaneously turned angularly by a first predetermined angle, such that the lengthwise line is offset from the Z-axis by a first offset angle which is equal to the first predetermined angle. The bridging rail member has an arc segment which extends in a circumferential direction about the origin, and two end segments which flank the arc segment, and which are secured to the two ring members, respectively, such that the arc segment and the two end segments cooperatively define a reference plane. The movable bracket is mounted slidably on the arc segment, and defines a radially oriented index line, which is parallel to the lengthwise line of the instrument in an initial position. The movable bracket, according to the coordinate of the target, is slid relative to the origin by a second predetermined angle, such that the lengthwise line is further offset from the Z-axis by a second offset angle, which is equal to the second predetermined angle. The swivel member defines a central plane, and has a distal end and a proximate end which is swivel-mounted on the movable bracket about a swivel axis normal to the reference plane so as to permit the swivel member to swivel from a starting position, where the radially oriented index line is within the central plane, to an ending position, where the central plane intersects with the radially oriented index line by a first compensation angle to compensate for the second offset angle. The instrument holder is configured to hold the instrument, and has an outward end and an inward end which is opposite to the outward end along the lengthwise line, and which is hinged to the distal end of the swivel member about a hinge axis within the reference plane, such that the outward end of the instrument holder is turned about the hinge axis by a second compensation angle to compensate for the first offset angle so as to permit the instrument to be guided toward the target along the lengthwise line parallel to the Z-axis.

BRIEF DESCRIPTION OF THE DRAWINGS

Other features and advantages of the disclosure will become apparent in the following detailed description of the embodiment with reference to the accompanying drawings, in which.

DETAILED DESCRIPTION

Figure 1:
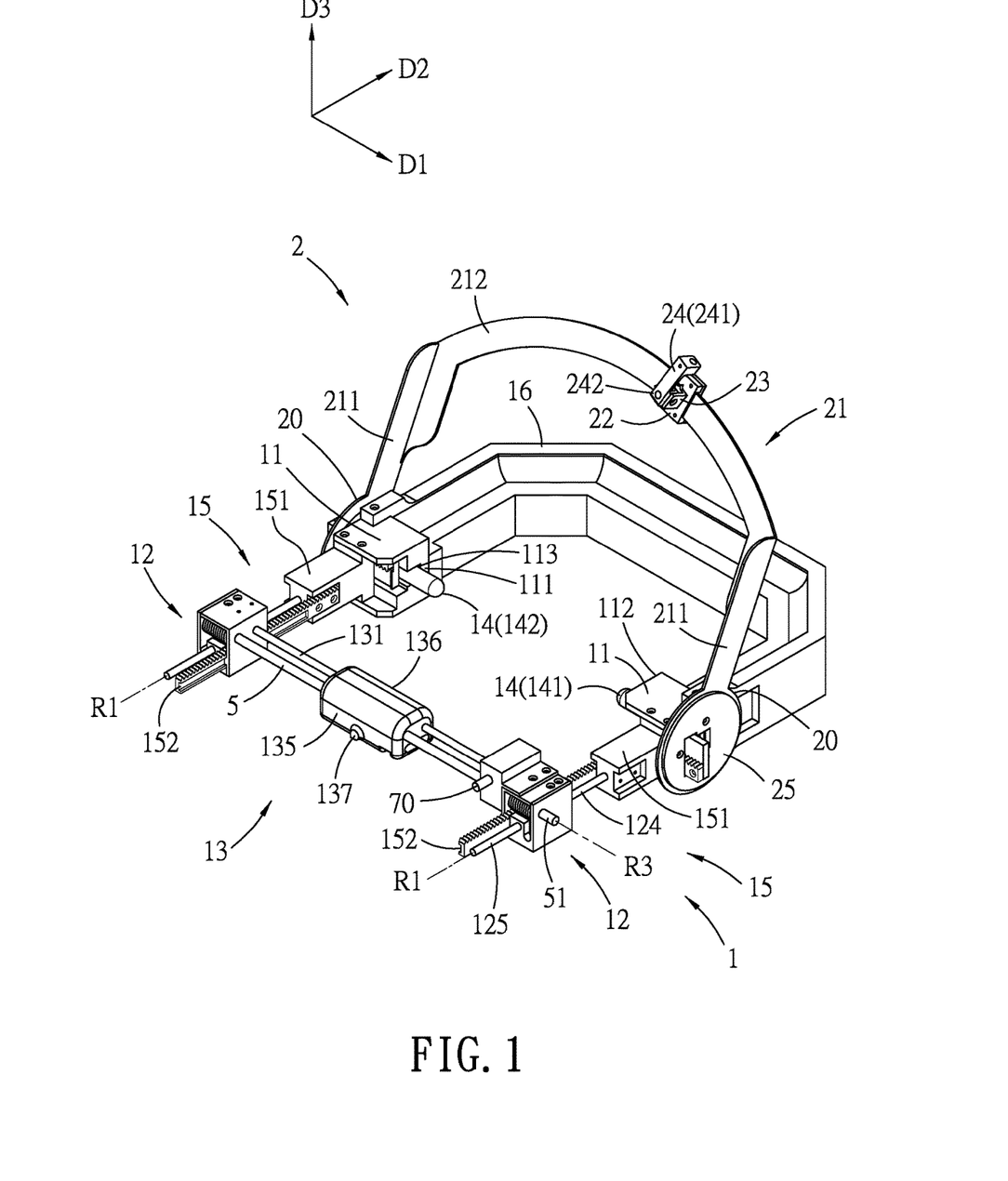
FIG. 1 is a perspective view of a noninvasive stereotactic assembly according to an embodiment of the disclosure.
Figure 5:
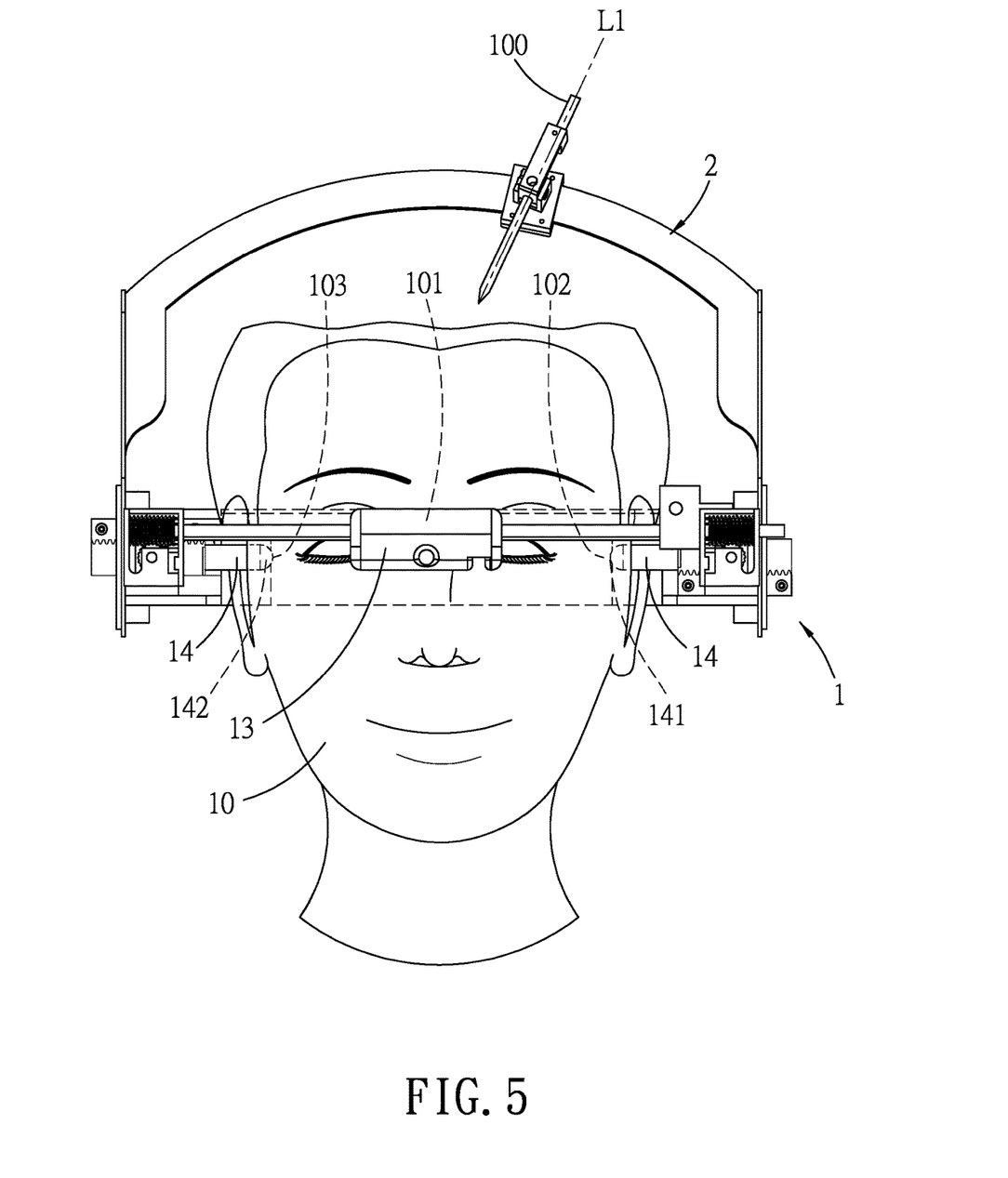
FIG. 5 is a schematic view illustrating when the noninvasive stereotactic assembly is secured on the patient's head.
Figure 6:
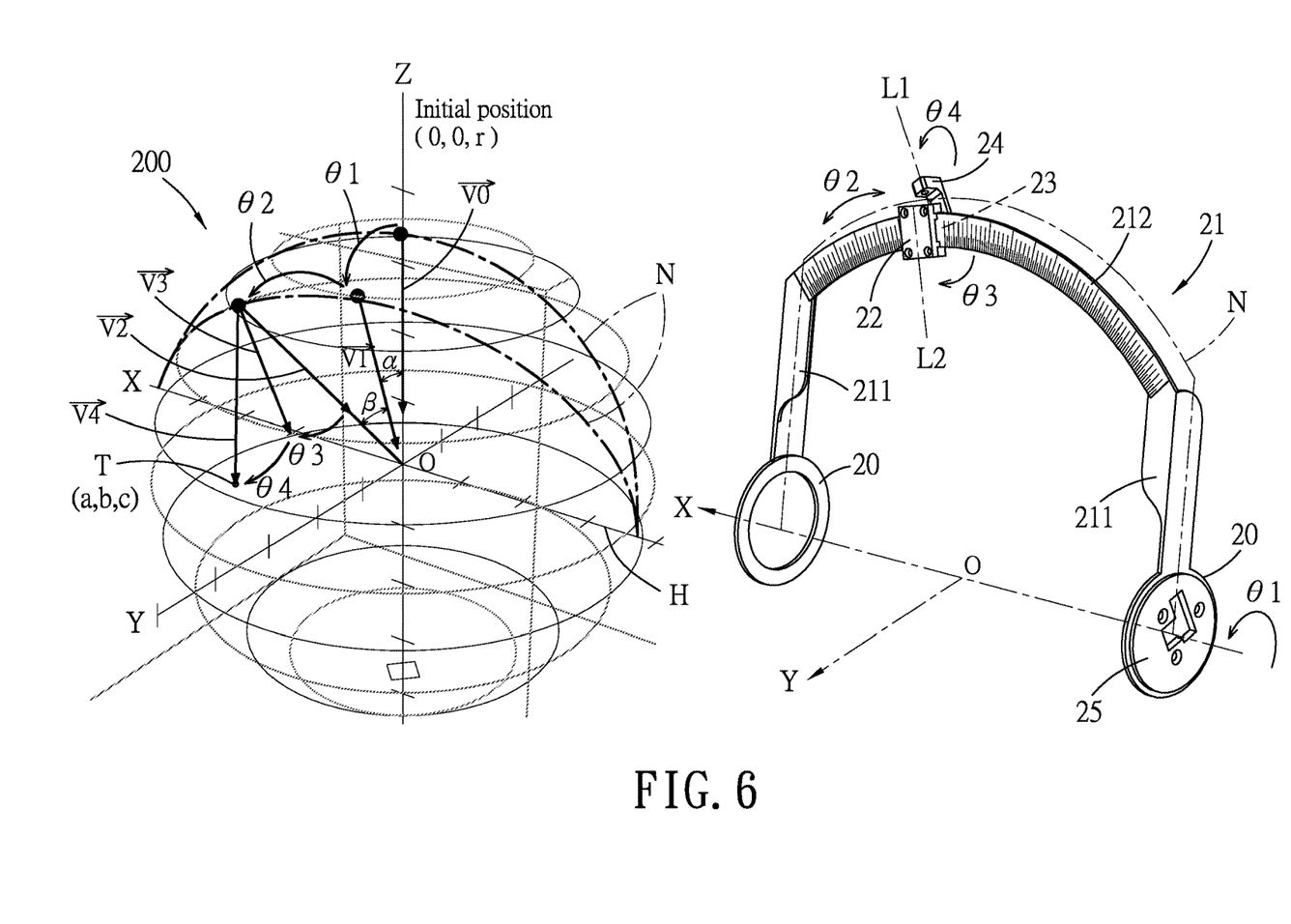
FIG. 6 illustrates that orientations of an instrument varies in a three-dimensional coordinate system in response to operations of an instrument positioning subassembly of the noninvasive stereotactic assembly.

With reference to FIGS. 1, 5, and 6, a noninvasive stereotactic assembly for guiding an instrument 100 to a target (T) within a patient's head 10 according to an embodiment of the disclosure is shown to include a head frame subassembly 1 and an instrument positioning subassembly 2. As shown in FIG. 5, the patient's head 10 includes a nasion 101 and left and right temporal bones 102, 103. The target (T) shown in FIG. 6 has a coordinate (a, b, c) determined by a three-dimensional coordinate system 200 of image data of the patient's head 10. The instrument 100 defines a lengthwise line (L1) which is initially oriented along a Z-axis toward an origin (0) of the three-dimensional coordinate system 200. As shown in FIG. 6, the lengthwise line (L1) of the instrument 100 is initially shown by a vector $\vec{V0}$. The instrument 100 may be, for example, a biopsy needle, or deep brain stimulation (DBS) leads or electrodes.

The head frame subassembly 1 includes a pair of seat blocks 11, a pair of adjusting units 12, a nasion positioning member 13, a pair of adjustable pin members 14, and a pair of cantilever units 15.

Figure 2:
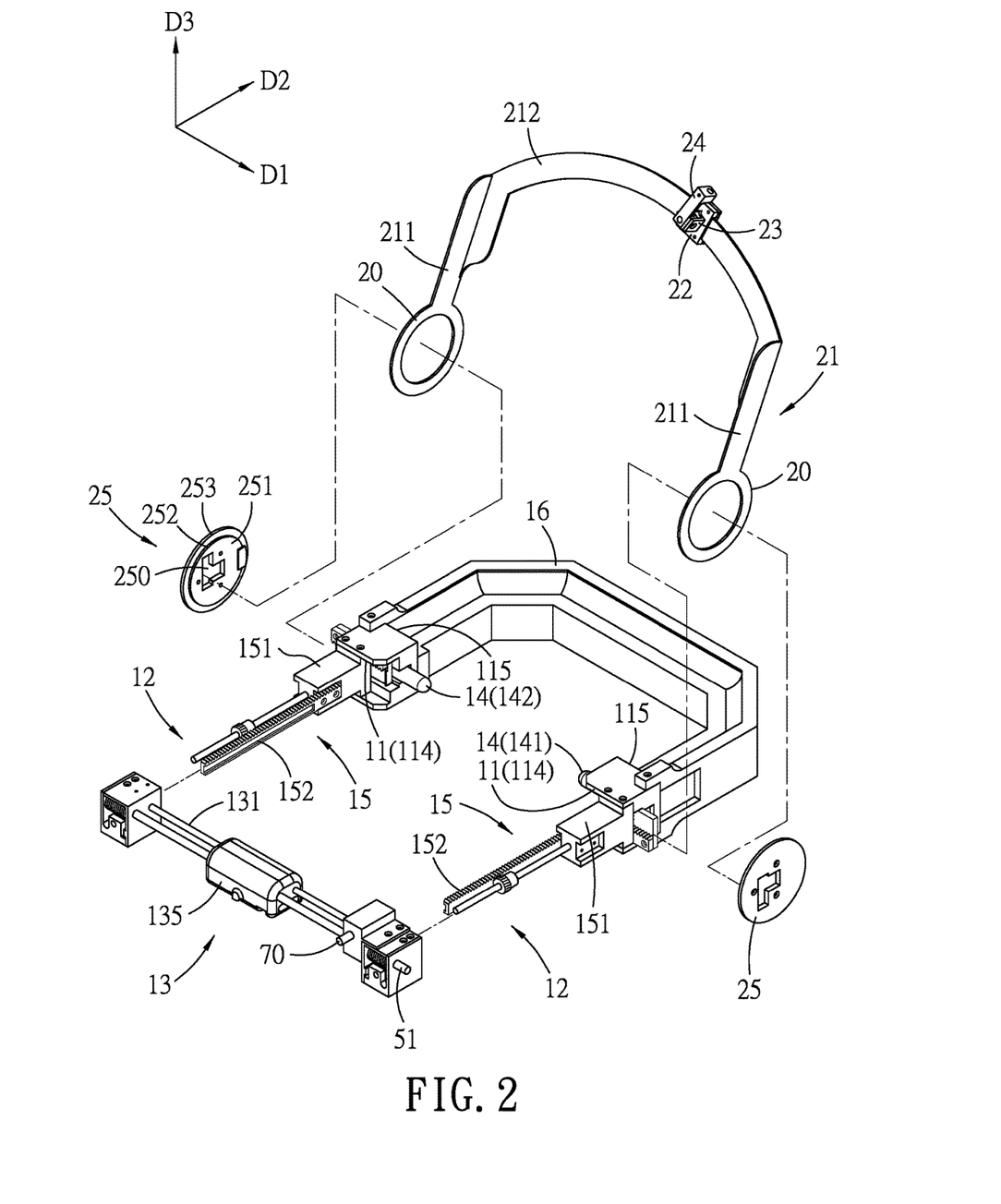
FIG. 2 is a partial exploded perspective view of the noninvasive stereotactic assembly.
Figure 4:
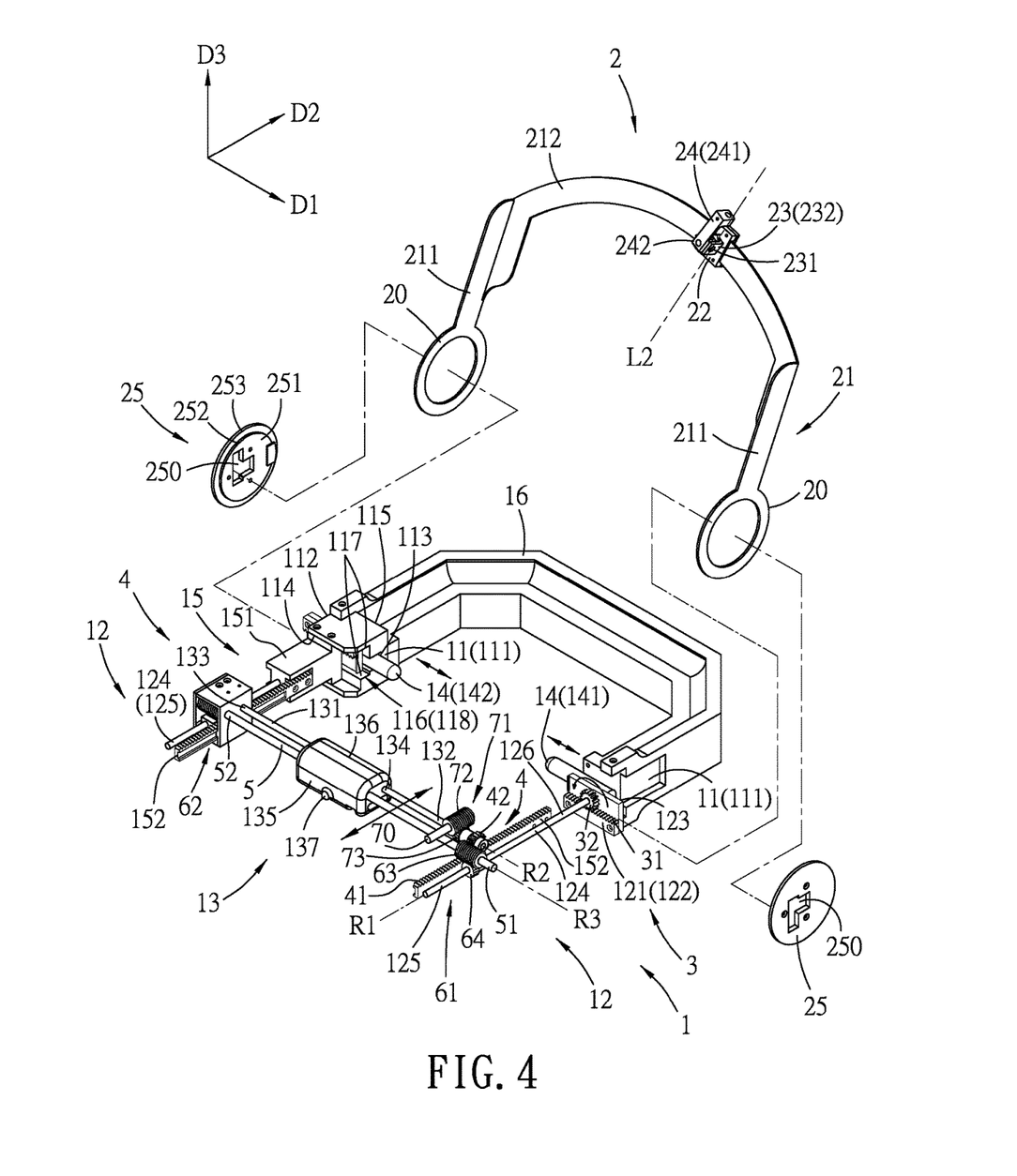
FIG. 4 is still another partial exploded perspective view of the noninvasive stereotactic assembly with some parts omitted.

As shown in FIGS. 1, 2, and 4, the seat blocks 11 are spaced apart from each other in a left-and-right direction (D1). Each of the seat blocks 11 has left and right surfaces 111, 112 and is formed with a guiding slot 113 which extends through the left and right surfaces 111, 112. In this embodiment, each of the seat blocks 11 has front and rear surfaces 114, 115 opposite to each other in an anterior-and-posterior direction (D2). The front surface 114 has an open groove 116 which extends toward the rear surface 115 to be in spatial communication with the guiding slot 113, and which extends along a direction (D3) of the Z-axis to terminate at two end walls 117 that cooperatively define a slideway 118 therebetween.

As shown in FIGS. 1, 2, 4, and 5, the adjustable pin members 14 are slidably and respectively mounted in the guiding slots 113 of the seat blocks 11, and have respectively left and right pointed ends 141, 142 that are adapted to extend into left and right ear canals of the patient's head 10 to be brought into rigid engagement with the left and right temporal bones 102, 103, respectively, so as to cooperatively define an X-axis of the three-dimensional coordinate system 200 (see also FIG. 6). Alternatively, the adjustable pin members 14 may be brought into rigid engagement with, for example, left and right zygomatic bones (not shown) of the patient, respectively.

The nasion positioning member 13 includes a beam body 131 and a nasion pad 135.

As shown in FIG. 4, the beam body 131 extends in the left-and-right direction (D1) to terminate at left and right actuated end segments 132, 133, and has a mid segment 134 between the left and right actuated end segments 132, 133. In this embodiment, the beam body 131 is configured to be driven to rotate relative to the nasion pad 135 about a beam axis (R2) in the left-and-right direction (D1).

The nasion pad 135 is mounted on the mid segment 134 of the beam body 131, and has a mid area 136 and an index protrusion 137. The mid area 136 is adapted to be brought into rigid engagement with the nasion 101 of the patient. The index protrusion 137 is opposite to and in line with the mid area 136 in the anterior-and-posterior direction (D2). When the mid area 136 is in rigid engagement with the nasion 101 of the patient, the index protrusion 137 and the mid area 136 cooperatively defines a Y-axis of the three-dimensional coordinate system 200, which intersects with the X-axis to define the origin (0) (see also FIG. 6). Alternatively, the nasion pad 135 may be brought into rigid engagement with, for example, an upper dentition (not shown) of the patient.

Each of the cantilever units 15 includes a cantilever block 151 and a cantilever arm 152. The cantilever block 151 is secured to a corresponding one of the seat blocks 11. The cantilever arm 152 extends from the cantilever block 151 in the anterior-and-posterior direction (D2), and is configured to permit a corresponding one of the left and right actuated end segments 132, 133 to be adjustably moved along the anterior-and-posterior direction (D2).

Each of the adjusting units 12 is coupled to a corresponding one of the adjustable pin members 14 so as to permit the adjustable pin members 14 to move toward or away from each other. In this embodiment, as best shown in FIG. 4, each of the adjusting units 12 includes a slider 121, a driven rod 124, and a first rack- and pinion mechanism 3.

The slider 121 is slidably mounted on the slideway 118 of a corresponding one of the seat blocks 11, and has a forward surface 122 and a rearward surface 123 opposite to the forward surface 122 in the anterior-and-posterior direction (D2). The rearward surface 123 is secured to a corresponding one of the adjustable pin members 14 to permit the corresponding one of the adjustable pin members 14 to move with the slider 121.

The driven rod 124 is coupled to be driven to rotate about a rotating axis (R1) in the anterior-and-posterior direction (D2), and has a front end segment 125 and a rear end segment 126. The front end segment 125 is disposed outboard of the cantilever arm 152 of a corresponding one of the cantilever units 15. The rear end segment 126 is rotatably mounted in the cantilever block 151 of a corresponding one of the cantilever units 15 about the rotating axis (R1).

The first rack-and-pinion mechanism 3 is disposed to couple the rear end segment 126 of the driven rod 124 with the forward surface 122 of the slider 121 so as to translate rotation of the driven rod 124 into linear movement of the slider 121. As shown in FIG. 4, the first rack-and-pinion mechanism 3 includes a first rack 31 formed on the forward surface 122 of the slider 121, and a first pinion 32 which is secured on the rear end segment 126 of the driven rod 124, and which is meshed with the first rack 31.

As shown in FIG. 4, the head frame subassembly 1 further includes a pair of second rack-and-pinion mechanisms 4, a drive rod 5, a left worm-drive mechanism 61, a right worm-drive mechanism 62, an operating rod 70, and a front worm-drive mechanism 71.

Each of the second rack-and-pinion mechanisms 4 is disposed to couple a corresponding one of the left and right actuated end segments 132, 133 of the beam body 131 with the cantilever arm 152 of a corresponding one of the cantilever units 15 so as to translate rotation of the beam body 131 into linear movement of the nasion pad 135 in the anterior-and-posterior direction (D2). In this embodiment, each of the second rack-and-pinion mechanisms 4 includes a second rack 41 formed on the cantilever arm 152 of a corresponding one of the cantilever unit 15, and a second pinion 42 which is secured on a corresponding one of the left and right actuated end segments 132, 133 of the beam body 131, and which is meshed with the second rack 41.

The drive rod 5 extends in the left-and-right direction (D1) through the nasion pad 135 to terminate at left and right drive end segments 51, 52, and is rotatable relative to the nasion pad 135 about a rod axis (R3) parallel to the beam axis (R2).

Each of the left and right worm-drive mechanisms 61, 62 is disposed to couple a corresponding one of the left and right drive end segments 51, 52 of the drive rod 5 with the front end segment 125 of the driven rod 124 of a corresponding one of the adjusting units 12 so as to synchronize rotations of the driven rods 124 of the adjusting units 12. The left and right worm-drive mechanisms 61, 62 are configured such that when the drive rod 5 is rotated, one of the driven rods 124 of the adjusting units 12 is driven to rotate in a clockwise direction, and the other one of the driven rods 124 of the adjusting units 12 is driven to rotate in a counter-clockwise direction so as to drive the adjustable pin members 14 to move toward or away from each other.

As shown in FIG. 4, in this embodiment, each of the left and right worm-drive mechanisms 61, 62 includes a worm screw 63 and a worm gear 64. The worm screw 63 is secured on a corresponding one of the left and right drive end segments 51, 52 of the drive rod 5. The worm gear 64 is in mesh engagement with the worm screw 63, and is configured to be in splined engagement with the front end segment 125 of the driven rod 124 of a corresponding one of the adjusting units 12 such that in response to linear movement of the nasion pad 135 in the anterior-and-posterior direction (D2), the worm gear 64 is dragged by the worm screw 63 to slide on the driven rod 124 of a corresponding one of the adjusting units 12 in the anterior-and-posterior direction (D2).

The operating rod 70 is disposed above the beam body 131. The front worm-drive mechanism 71 is disposed to couple the operating rod 70 with the beam body 131 so as to translate rotation of the operating rod 70 into rotation of the beam body 131. The front worm-drive mechanism 71 includes a front worm screw 72 secured on the operating rod 70, and a front worm gear 73 which is meshed with the front worm screw 72, and which is secured on the beam body 131.

In this embodiment, the head frame subassembly 1 further includes a rearward frame 16 which interconnects the rear surfaces 115 of the seat blocks 11, and which is configured to counterbalance the nasion positioning member 13, so as to keep the left and right pointed ends 141, 142 and the index protrusion 137 within a horizontal plane (H), thereby enhancing the accuracy performance of the three-dimensional coordinate system 200. In this embodiment, the horizontal plane (H) defines an X-Y plane of the three-dimensional coordinate system 200.

As shown in FIGS. 1 to 4, the instrument positioning subassembly 2 includes two ring members 20, a bridging rail member 21, a movable bracket 22, a swivel member 23, and an instrument holder 24.

The two ring members 20 are mounted rotatably on and outboard of the seat blocks 11 about the X-axis, respectively. According to the coordinate (a, b, c) of the target (T) (see also FIG. 6), the two ring members 20 are simultaneously turned angularly by a first predetermined angle (θ1), such that the lengthwise line (L1) is offset from the Z-axis by a first offset angle (α) which is equal to the first predetermined angle (θ1). At this moment, the lengthwise line (L1) shown in FIG. 6 is represented by a vector $\vec{V1}$.

The bridging rail member 21 has an arc segment 212 and two end segments 211. The arc segment 212 extends in a circumferential direction about the origin (0). The two end segments 211 flank the arc segment 212, and are secured to the two ring members 20, respectively. The arc segment 212 and the two end segments 211 cooperatively define a reference plane (N). The reference plane (N) is initially arranged in an X-Z plane, as shown in FIG. 6.

The movable bracket 22 is mounted slidably on the arc segment 212, and defines a radially oriented index line (L2), which is parallel to the lengthwise line (L1) of the instrument 100 in an initial position. According to the coordinate (a, b, c) of the target (T), the movable bracket 22 is slid relative to the origin (0) by a second predetermined angle (θ2), such that the lengthwise line (L1) is further offset from the Z-axis by a second offset angle (β), which is equal to the second predetermined angle (θ2). At this moment, as shown in FIG. 6, the lengthwise line (L1) is represented by a vector $\vec{V2}$.

Figure 7:
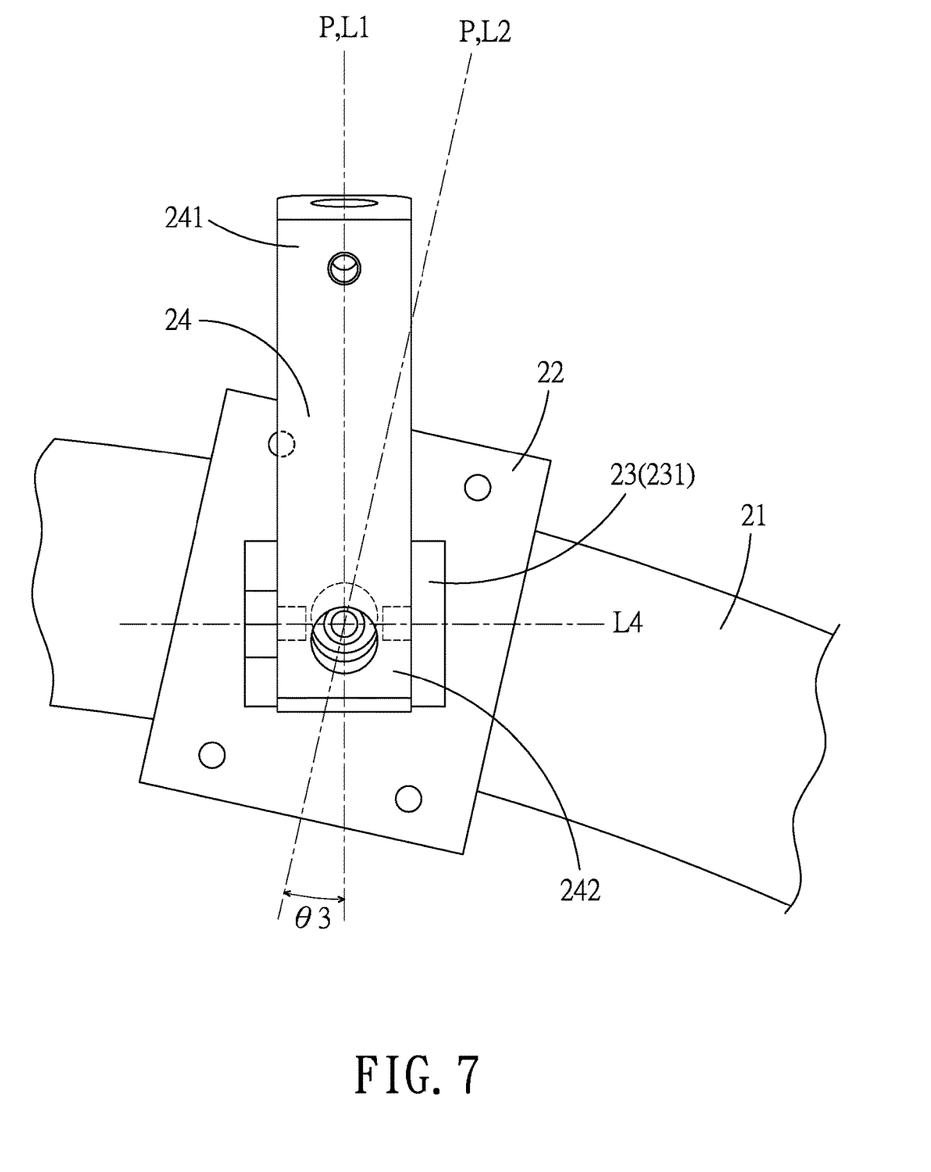
FIG. 7 is a fragmentary enlarged view illustrating a swivel movement of a swivel member of the instrument positioning subassembly relative to a radially oriented index line of a movable bracket.
Figure 8:
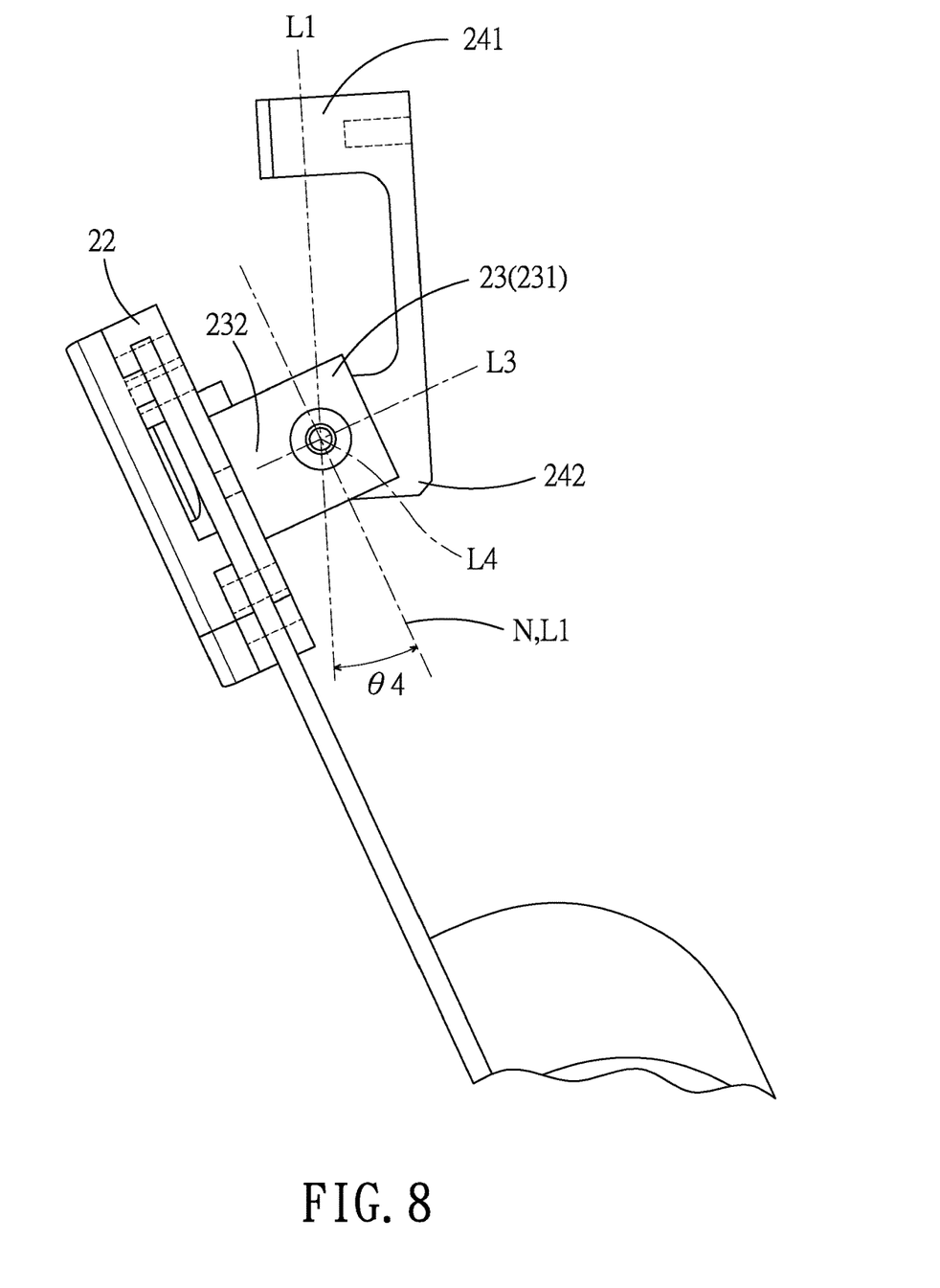
FIG. 8 is a fragmentary enlarged view illustrating a hinge movement of an instrument holder of the instrument positioning subassembly relative to a reference plane.

The swivel member 23 defines a central plane (P) as best shown in FIG. 7, and has a distal end 231 and a proximate end 232 (see FIGS. 4 and 8). The proximate end 232 is swivel-mounted on the movable bracket 22 about a swivel axis (L3) normal to the reference plane (N) so as to permit the swivel member 23 to swivel from a starting position, where the radially oriented index line (L2) is within the central plane (P), to an ending position, where the central plane (P) intersects with the radially oriented index line (L2) by a first compensation angle (θ3) to compensate for the second offset angle (β). In the starting position, the central plane (P) and the radially oriented index line (L2) shown in FIG. 7 are represented by the same solid line, and the lengthwise line shown in FIG. 6 is represented by the vector $\vec{V2}$. In the ending position, the central plane (P) in FIG. 7 is represented by a phantom line, the radially oriented index line (L2) in FIG. 7 is still represented by the solid line, and the lengthwise line (L1) in FIG. 6 is represented by a vector $\vec{V3}$.

The instrument holder 24 is configured to hold the instrument 100, and has an outward end 241 and an inward end 242. As best shown in FIG. 8, the inward end 242 is opposite to the outward end 241 along the lengthwise line (L1), and is hinged to the distal end 231 of the swivel member 23 about a hinge axis (L4) within the reference plane (N). The lengthwise line (L1) is initially within the reference plane (N), as represented by the solid line in FIG. 8. The outward end 241 of the instrument holder 24 is turned about the hinge axis (L4) by a second compensation angle (θ4) to compensate for the first offset angle (α) so as to permit the instrument 100 to be guided toward the target (T) along the lengthwise line (L1) parallel to the Z-axis. At this moment, the lengthwise line (L1) is represented in FIG. 8 by a phantom line, and is represented in FIG. 6 by a vector $\vec{V4}$.

Figure 3:
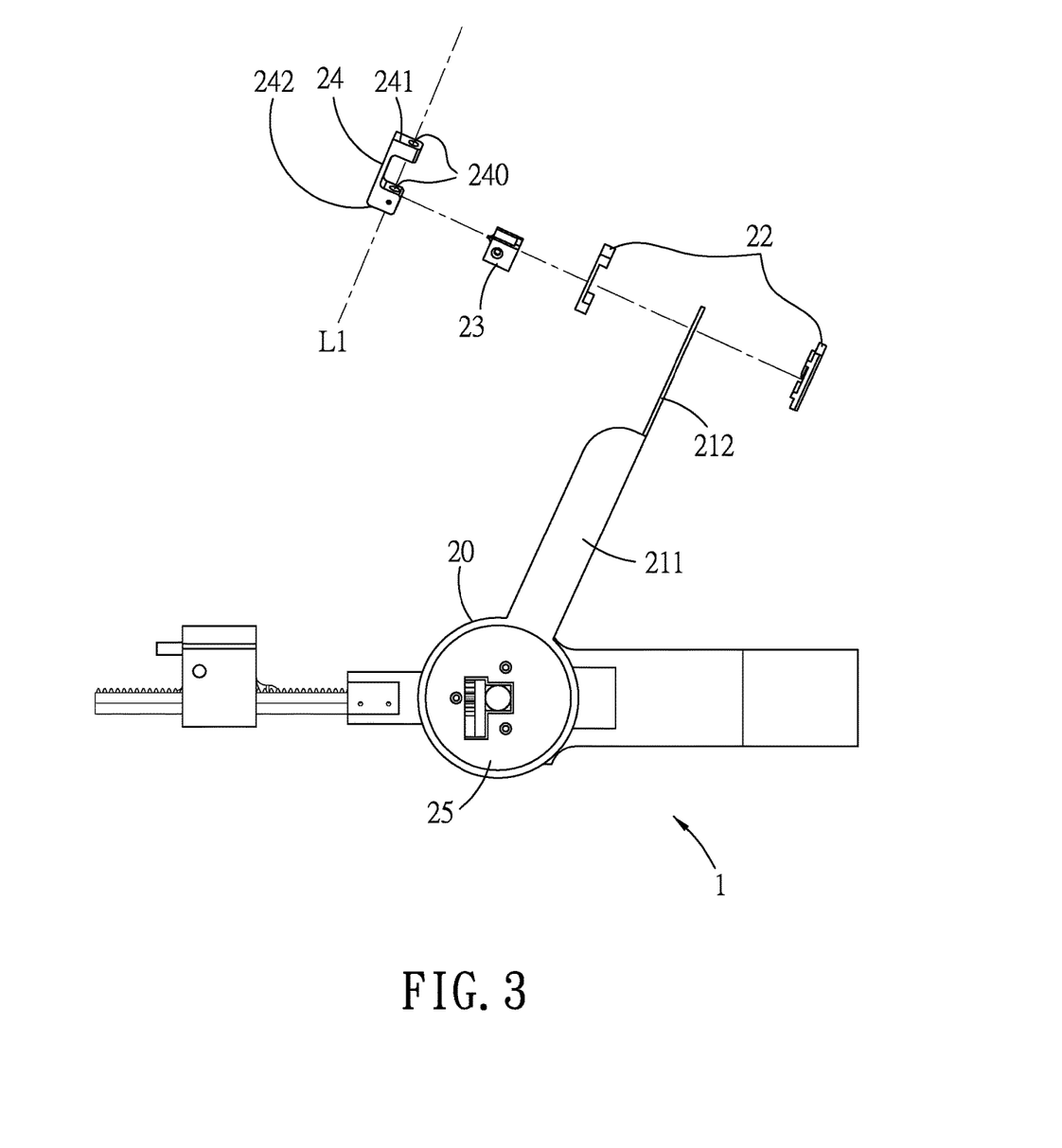
FIG. 3 is another partial exploded side view of the noninvasive stereotactic assembly.

In this embodiment, as shown in FIGS. 3 and 5, the outward and inward ends 241, 242 have respectively instrument retaining holes 240 which are in line with each other along the lengthwise line (L1), and which are configured to cooperatively retain the instrument 100.

In this embodiment, the instrument positioning subassembly 2 further includes a pair of circular side covers 25 disposed outboard of the ring members 20, respectively. Each of the circular covers 25 has a wheel body 251 and an annular flange 253.

The wheel body 251 has a rim surface 252 and is formed with a through hole 250 configured to permit extension of a corresponding one of the adjustable pin members 14 and the slider 121 of a corresponding one of the adjusting units 12. The rim surface 252 is configured to be in fitting engagement with a corresponding one of the ring members 20 so as to permit the corresponding one of the ring members 20 to be rotatably mounted thereon.

The annular flange 253 extends radially from an outer edge of the rim surface 252 so as to prevent a corresponding one of the ring members 20 from falling off.

In operation, after a patient wears the noninvasive stereotactic assembly on his/her head, an operator may grip the left drive end segment 51 to rotate the drive rod 5 to adjust the position of the adjustable pin members 14 so as to bring the left and right pointed ends 141, 142 into rigid engagement with the left and right temporal bones 102, 103 of the patient, respectively.

Thereafter, the operator may rotate the operating rod 70 to drive the nasion positioning member 13, together with the drive rod 5 and the left and right worm-drive mechanism 61, 62, to move in the anterior-and-posterior direction (D2) to thereby bring the middle area 136 of the nasion pad 135 into rigid engagement with the nasion 101 of the patient.

Next, the patient with the noninvasive stereotactic assembly in place is subjected to a computerized tomography (CT) scan or a magnetic resonance imaging (MRI) scan. The coordinate (a, b, c) of the target (T) relative to the noninvasive stereotactic assembly can be determined in the three-dimensional coordinate system 200 of the image data of the patient's head 10 using existing computer software. According to the coordinate of the target, the displacing angles (θ1, θ2, θ3, θ4) of the ring members 20, the movable bracket 22, the swivel member 23, and the instrument holder 24 can be also computed using computer software.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A noninvasive stereotactic assembly for guiding an instrument to a target within a patient's head which includes a nasion and left and right temporal bones, the target having a coordinate determined by a three-dimensional coordinate system of image data of the patient's head, the instrument defining a lengthwise line which is initially oriented along a Z-axis toward an origin of the three-dimensional coordinate system, said stereotactic assembly comprising:

a head frame subassembly including
a pair of seat blocks which are spaced apart from each other in a left-and-right direction, each of said seat blocks having left and right surfaces and being formed with a guiding slot which extends through said left and right surfaces,
a pair of adjustable pin members which are slidably and respectively mounted in said guiding slots of said seat blocks, and which have respectively left and right pointed ends that are adapted to be brought into rigid engagement with the left and right temporal bones, respectively, so as to cooperatively define an X-axis of the three-dimensional coordinate system,
a nasion positioning member including
a beam body which extends in the left-and-right direction to terminate at left and right actuated end segments, and
a nasion pad which is mounted on a mid segment of said beam body between said left and right actuated end segments, and which has a mid area adapted to be brought into rigid engagement with the nasion of the patient, and an index protrusion opposite to and in line with said mid area in an anterior-and-posterior direction, such that when said mid area is in rigid engagement with the nasion of the patient, said index protrusion and said mid area cooperatively defines a Y-axis of the three-dimensional coordinate system, which intersects with the X-axis to define the origin,
a pair of cantilever units each including
a cantilever block secured to a corresponding one of said seat blocks, and
a cantilever arm which extends from said cantilever block in the anterior-and-posterior direction, and which is configured to permit a corresponding one of said left and right actuated end segments to be adjustably moved along the anterior-and-posterior direction, and
a pair of adjusting units each of which is coupled to a corresponding one of said adjustable pin members so as to permit said adjustable pin members to move toward or away from each other; and
an instrument positioning subassembly including
two ring members which are mounted rotatably on and outboard of said seat blocks about the X-axis, respectively, and which, according to the coordinate of the target, are simultaneously turned angularly by a first predetermined angle, such that the lengthwise line is offset from the Z-axis by a first offset angle which is equal to the first predetermined angle, a bridging rail member having an arc segment which extends in a circumferential direction about the origin, and two end segments which flank said arc segment, and which are secured to said two ring members, respectively, such that said arc segment and said two end segments cooperatively define a reference plane, a movable bracket mounted slidably on said arc segment, and defining a radially oriented index line, which is parallel to the lengthwise line of the instrument in an initial position, said movable bracket, according to the coordinate of the target, being slid relative to the origin by a second predetermined angle, such that the lengthwise line is further offset from the Z-axis by a second offset angle, which is equal to the second predetermined angle, a swivel member defining a central plane, and having a distal end and a proximate end which is swivel-mounted on said movable bracket about a swivel axis normal to said reference plane so as to permit said swivel member to swivel from a starting position, where said radially oriented index line is within said central plane, to an ending position, where said central plane intersects with said radially oriented index line by a first compensation angle to compensate for the second offset angle, and an instrument holder configured to hold the instrument, and having an outward end and an inward end which is opposite to said outward end along the lengthwise line, and which is hinged to said distal end of said swivel member about a hinge axis within said reference plane, such that said outward end of said instrument holder is turned about the hinge axis by a second compensation angle to compensate for the first offset angle so as to permit the instrument to be guided toward the target along the lengthwise line parallel to the Z-axis.

2. The noninvasive stereotactic assembly according to claim 1, wherein:

each of said seat blocks has front and rear surfaces opposite to each other in the anterior-and-posterior direction, said front surface having an open groove which extends toward said rear surface to be in spatial communication with said guiding slot, and which extends along a direction of the Z-axis to terminate at two end walls that cooperatively define a slideway therebetween;

each of said adjusting units includes a slider which is slidably mounted on said slideway of a corresponding one of said seat blocks, and which has a forward surface and a rearward surface that is opposite to said forward surface in the anterior-and-posterior direction and that is secured to a corresponding one of said adjustable pin members to permit the corresponding one of said adjustable pin members to move with said slider, a driven rod which is coupled to be driven to rotate about a rotating axis in the anterior-and-posterior direction, and which has a front end segment disposed outboard of said cantilever arm of a corresponding one of said cantilever units, and a rear end segment which is rotatably mounted in said cantilever block of a corresponding one of said cantilever units about the rotating axis, and a first rack-and-pinion mechanism disposed to couple said rear end segment of said driven rod with said forward surface of said slider so as to translate rotation of said driven rod into linear movement of said slider;

said beam body is configured to be driven to rotate relative to said nasion pad about a beam axis in the left-and-right direction;

said head frame subassembly further includes a pair of second rack-and-pinion mechanisms each of which is disposed to couple a corresponding one of said left and right actuated end segments of said beam body with said cantilever arm of a corresponding one of said cantilever units so as to translate rotation of said beam body into linear movement of said nasion pad in the anterior-and-posterior direction, a drive rod which extends in the left-and-right direction through said nasion pad to terminate at left and right drive end segments, and which is rotatable relative to said nasion pad about a rod axis parallel to the beam axis, and a left worm-drive mechanism and a right worm-drive mechanism, each of which is disposed to couple a corresponding one of said left and right drive end segments of said drive rod with said front end segment of said driven rod of a corresponding one of said adjusting units so as to synchronize rotations of said driven rods of said adjusting units, said left and right worm-drive mechanisms being configured such that when said drive rod is rotated, one of said driven rods of said adjusting units is driven to rotate in a clockwise direction, and the other one of said driven rods of said adjusting units is driven to rotate in a counterclockwise direction.

3. The noninvasive stereotactic assembly according to claim 2, wherein each of said left and right worm-drive mechanisms includes a worm screw secured on a corresponding one of said left and right drive end segments of said drive rod, and a worm gear which is in mesh engagement with said worm screw, and which is configured to be in splined engagement with said front end segment of said driven rod of a corresponding one of said adjusting units such that in response to linear movement of said nasion pad in the anterior-and-posterior direction, said worm gear is dragged by said worm screw to slide on said driven rod of a corresponding one of said adjusting units in the anterior-and-posterior direction.

4. The noninvasive stereotactic assembly according to claim 2, wherein said head frame subassembly further includes an operating rod disposed above said beam body, and a front worm-drive mechanism disposed to couple said operating rod with said beam body so as to translate rotation of said operating rod into rotation of said beam body.

5. The noninvasive stereotactic assembly according to claim 1, wherein said head frame subassembly further includes a rearward frame which interconnects said rear surfaces of said seat blocks, and which is configured to counterbalance said nasion positioning member, so as to keep said left and right pointed ends and said index protrusion within a horizontal plane, thereby enhancing the accuracy performance of the three-dimensional coordinate system.

6. The noninvasive stereotactic assembly according to claim 1, wherein said instrument positioning subassembly further includes a pair of circular side covers disposed outboard of said ring members, respectively, each of said circular covers having
- a wheel body which is formed with a through hole configured to permit extension of a corresponding one of said adjustable pin members and a slider of a corresponding one of said adjusting units, and which has a rim surface configured to be in fitting engagement with a corresponding one of said ring members so as to permit the corresponding one of said ring members to be rotatably mounted thereon, and
- an annular flange extending radially from an outer edge of said rim surface so as to prevent a corresponding one of said ring members from falling off.

* * * * *